United States Patent [19]

Chabala et al.

[11] Patent Number: 4,659,720

[45] Date of Patent: Apr. 21, 1987

[54] 5-AMINO OR SUBSTITUTED AMINO IMIDAZOLES USEFUL TO TREAT COCCIDIOSIS

[75] Inventors: John C. Chabala, Westfield; Michael H. Fisher, Ringoes; Arthur A. Patchett, Westfield, all of N.J.

[73] Assignee: Merck & Co., Inc., Rahway, N.J.

[21] Appl. No.: 551,150

[22] Filed: Nov. 16, 1983

Related U.S. Application Data

[63] Continuation-in-part of Ser. No. 450,848, Dec. 20, 1982, abandoned.

[51] Int. Cl.$^4$ .................... A61K 31/44; A61K 31/47; C07D 401/04; C07D 401/06
[52] U.S. Cl. .................... 514/313; 514/314; 514/341; 514/386; 514/392; 514/398; 514/400; 546/162; 546/176; 546/278; 548/301; 548/315; 548/319; 548/337; 548/343
[58] Field of Search ............. 548/315, 319, 301, 337, 548/343; 546/162, 176, 278; 424/258, 263, 273 R; 514/392, 398, 386, 400, 313, 314, 341

[56] References Cited

U.S. PATENT DOCUMENTS 3,959,305 5/1976 Ainsworth et al. ............. 548/301
4,191,554 3/1980 Gregory ............................ 71/95
4,265,900 5/1981 Rasmussen et al. ............. 548/315

FOREIGN PATENT DOCUMENTS 112861 9/1979 Japan ............................... 548/343

OTHER PUBLICATIONS

Sax et al., J. Org. Chem., 25, pp. 1590–1595, 1960.
Vingiello et al., J. Org. Chem., 25, pp. 2091–2094, 1960.
Paloson et al., J. Amer. Chem. Soc., 92, pp. 336–343, 1970.
Chemical Abstracts 25, 1816, to Oesterlin, (1931).
Chemical Abstracts 55, 8334b, (1961).
Chemical Abstracts 41, 1642f to Chardonnens, (1947).
Helv. Chim. Acta. 29, 1413 (1946).
Chemical Abstracts 30, 1046$^4$, (1936).
Chemical Abstracts 30, 5965$^4$, (1936).
Chemical Abstracts 72, 132238e (1970).
Chemical Abstracts 55, 9339f, (1961).
Chemical Abstracts 53, 16145g, (1959).
Chemical Abstracts 45, 7075d, (1951).
Chemical Abstracts 67, 14421b, (1964).
Chemical Abstracts, 10122 (1959).
Chemical Abstracts 59, 3791f, (1963).
Chemical Abstracts 37, 4707$^4$, (1943).
Chem. Ind. 213 (1972).
Chem. Rev., 63, 489 (1963).
Chemical Abstracts 96, 68990K (1982)–Sumitomo.
Chemical Abstracts 96, 142826e (1982–Kaufmann et al.
Chemical Abstracts 94, 103363r (1981)–Pfizer.
Chemical Abstracts 97, 216 195t (1982) Sankyo.

Primary Examiner—Henry H. Jiles
Assistant Examiner—Kurt G. Briscoe
Attorney, Agent, or Firm—David L. Rose

[57] ABSTRACT

5-Amino or substituted amino imidazoles are disclosed as having anticoccidial activity. The compounds are useful for controlling cecal and or intestinal coccidiosis when administered in minor quantitites to animals, in particular to poultry, usually in admixture with animal sustenance.

13 Claims, No Drawings

5-AMINO OR SUBSTITUTED AMINO IMIDAZOLES USEFUL TO TREAT COCCIDIOSIS

CROSS REFERENCE TO RELATED APPLICATIONS

This application is a continuation-in-part of our copending application Ser. No. 450,848 filed Dec. 20, 1982, now abandoned.

BACKGROUND OF THE INVENTION

This invention relates to new chemical compounds and the method of the preparation of the same. It relates further to the use of such new compounds for treating and preventing coccidiosis. This invention still more particularly relates to novel 5-amino and substituted amino imidazole compounds and substituted derivatives thereof and the use of the same in the control and treatment of coccidiosis.

Coccidiosis is a wide-spread poultry disease which is produced by infections of protozoa of the genus Eimeria which causes severe pathology in the intestines and ceca of poultry. Some of the most significant of these species are *E. tenella, E. acervulina, E. necatrix, E. brunetti, E. maxima, E. mitis, E. mivati, E. hagani* and *E. praecox* This disease is generally spread by the birds picking up the infectious organism in droppings on contaminated litter or ground or by way of food or drinking water. The disease is manifested by hemorrhage, accumulation of blood in the ceca, passage of blood to the droppings, weakness and digestive disturbances. The disease often terminates in the death of the animal but the fowl which survive severe infections have had their market value substantially reduced as a result of the infection. Coccidiosis is therefore a disease of great economic importance and extensive work has been done to find new and improved methods for controlling and treating coccidial infections in poultry.

SUMMARY OF THE INVENTION

This invention is based on the discovery that certain novel 5-amino and substituted amino imidazoles as well as substituted derivatives thereof have a surprisingly and unexpectedly high degree of activity against coccidiosis of poultry. Administration of a small amount of at least one of these compounds preferably by combination with poultry feed is effective in preventing or greatly reducing the incidence of coccidiosis. The compounds are effective against both the cecal form (caused principally by *E. tenella*) and the intestinal forms (principally caused by *E. acervulina, E. brunetti, E. maxima* and *E. necatrix*). The coccidiostats of this invention are particularly effective against the species that cause cecal damage in addition to preventing the pathology caused by the coccidia. These compounds also exert an inhibitory effect on the oocysts by greatly reducing the number and or the sporulation of those produced.

The instant compounds are also active against Eimeria spp, in other animals.

The novel imidazole derivatives of this invention are prepared by reacting an appropriately substituted halide and a 1-unsubstituted imidazole compound in the presence of a base in a suitable reaction medium to obtain such novel 5-amino or substituted amino 1-substituted imidazoles.

It is therefore a primary object of this invention to provide novel 5-amino or substituted amino imidazoles with appropriate substitutions at the 1, 2, 3 and 4 positions which are useful in the control of coccidiosis. Still another object of this invention is to provide novel feed compositions useful for the prevention and supression of coccidiosis. A further object of this invention is to provide a new and useful method for the control of coccidiosis in poultry which comprises administering to the poultry minor amounts of the anti-coccidial substance of this invention. A still further object of this invention is to provide a method and alternate methods for preparing novel 5-amino and substituted amino imidazoles. These and further objects of this invention will become apparent from reading the following description.

DESCRIPTION OF THE INVENTION

The compounds of this invention are best realized in the following structural formula:

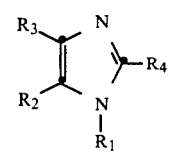

wherein: $R_1$ is mono-substituted phenyl or mono-substituted phenyl alkyl wherein the substituent is trifluoromethyl, loweralkanoyl, nitro, carboxy, carbalkoxy, acetamido, loweralkylthio, loweralkylsulfinyl, loweralkylsulfonyl or

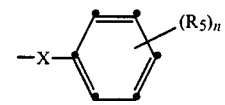

wherein n is from 1 to 5, $R_5$ is defined as below and X is O, S, SO, $SO_2$, $CH_2$, CO, CHOH, CHCN or $C=NR_6$ where $R_6$ is hydrogen loweralkyl, hydroxy, loweralkoxy, amino, loweralkylamino, or diloweralkylamino; $R_1$ is also polysubstituted phenyl or polysubstituted phenylalkyl wherein the substituents are two to five $R_5$ wherein $R_5$ chosen independently from any of halogen, cyano, trifluoromethyl, loweralkanoyl, nitro, loweralkyl, loweralkoxy, carboxy, carbalkoxy, trifluoromethoxy, acetamido, loweralkylthio, loweralkylsulfinyl, loweralkylsulfonyl, trichlorovinyl, trifluoromethylthio, trifluoromethylsulfinyl, or trifluoromethylsulfonyl or

where $R_5$, X, and n are as defined above.

Provided that if the monosubstituent or one of the polysubstituents is halogen, loweralkyl, or loweralkoxy, such groups are in positions other than those ortho to the position of attachment of the phenyl to the imidazole or the alkyl, which is in turn attached to the imidazole;

$R_1$ may also be phenacyl, pyridyl, pyridyl methyl, naphthyl, naphthylmethyl, quinolyl or quinolylmethyl;

$R_2$ is amino, mono or diloweralkyl amino, acetamido, acetimido, ureido, formamido, formimido or guanidino;

$R_3$ is carbamoyl, cyano, carbazoyl, amidino or N-hydroxycarbamoyl; and $R_4$ is hydrogen, loweralkyl, hydroxy, amino, mono- or diloweralkyl amino, phenyl, cyano, loweralkoxy, loweralkanoyloxy, loweralkylthio, loweralkylsulfinyl or loweralkylsulfonyl.

Compounds of the instant invention are realized in the foregoing structural formula wherein:

$R_1$ is monosubstituted phenyl or mono-substituted benzyl wherein the substituent is trifluoromethyl, phenoxy, benzoyl, phenylthio, phenylsulfinyl, phenylsulfonyl, halo, methyl or trifluoromethyl substituted phenoxy, halo, methyl or trifluoromethyl substituted phenylthio, halo, methyl or trifluoromethyl substituted phenyl sulfinyl, halo, methyl or trifluoromethyl substituted phenyl sulfonyl, or halo, methyl or trifluoromethyl substituted benzoyl or halo, methyl or trifluoromethyl substituted phenylhydroxymethyl;

$R_1$ is also di- or trisubstituted phenyl or di- or trisubstituted benzyl wherein the substituents are halogen, cyano, methyl, trifluoromethyl, phenoxy, benzoyl, phenylthio, phenylsulfinyl, phenylsulfonyl, halo, methyl or trifluoromethyl substituted phenoxy, halo, methyl or trifluoromethyl substituted phenylthio, halo, methyl or trifluoromethyl substituted phenylsulfinyl, halo, methyl or trifluoromethyl substituted phenylsulfonyl, halo, methyl or trifluoromethyl substituted benzoyl or halo, methyl or trifluoromethyl substituted phenylhydroxymethyl;

Provided that if the monosubstitutent or one of the substituents is halogen, such group is a position other then those ortho to the position of attachment of the phenyl to the imidazole or to the methylene which is in turn attached to the imidazole;

$R_2$ is amino or mono or diloweralkyl amino;

$R_3$ is carbamoyl; and $R_4$ is hydrogen.

Additional compounds of the instant invention are realized in the foregoing structural formula wherein $R_1$ is substituted phenyl or substituted benzyl wherein the substituents are 2 to 3 in the meta or para positions of halo, cyano, methyl or trifluoromethyl, halo, methyl or trifluoromethyl phenoxy, halo, methyl or trifluoromethyl phenylthio, halo, methyl or trifluoromethyl phenylsulfinyl, halo, methyl or trifluoromethyl phenylsulfonyl, halo, methyl or trifluoromethyl benzoyl or halo, methyl or trifluoromethyl substituted phenylhydroxymethyl;

$R_2$ is amino;

$R_3$ is carbamoyl; and $R_4$ is hydrogen.

The preferred compounds of the instant invention are realized in the foregoing structural formula wherein:

$R_1$ is monosubstituted phenyl or monosubstituted benzyl wherein the substituent is trifluoromethyl, phenoxy, benzoyl, phenylthio, phenylsulfinyl, phenylsulfonyl, halo or trifluoromethyl substituted phenoxy, halo or trifluoromethyl substituted phenylthio, halo or trifluoromethyl substituted phenyl sulfinyl, halo or trifluoromethyl substituted phenyl sulfonyl; or halo trifluoromethyl substituted benzoyl or halo, methyl or trifluoromethyl substituted phenylhydroxymethyl;

$R_1$ is also di- or trisubstituted phenyl or di- or trisubstituted benzyl wherein the substituents are halogen, cyano, methyl, trifluoromethyl, phenoxy, benzoyl, phenylthio, phenylsulfinyl, phenylsulfonyl, halo, methyl or trifluoromethyl substituted phenoxy, halo, methyl or trifluoromethyl substituted phenylthio, halo, methyl or trifluoromethyl substituted phenylsulfinyl, halo, methyl or trifluoromethyl substituted phenylsulfonyl, halo, methyl or trifluoromethyl substituted benzoyl or halo, methyl or trifluoromethyl substituted phenylhydroxymethyl;

Provided that if the monosubstituent or one of the substituents is halogen, such group is in a position other than those ortho to the position of attachment of the phenyl to the imidazole or to the methylene which is in turn attached to the imidazole;

$R_2$ is amino or mono or diloweralkyl amino;

$R_3$ is carbamoyl; and $R_4$ is hydrogen.

The most preferred compounds of the instant invention are realized in the foregoing structural formula wherein $R_1$ is substituted phenyl or substituted benzyl wherein the substituents are 2 to 3 in the meta or para positions of halo, cyano, methyl or trifluoromethyl, halo or trifluoromethyl phenoxy, halo or trifluoromethyl phenylthio, halo or trifluoromethyl phenylsulfinyl, halo or trifluoromethyl phenylsulfonyl, halo or trifluoromethyl benzoyl or halo, methyl or trifluoromethyl substituted phenylhydroxymethyl $R_2$ is amino;

$R_3$ is carbamoyl; and $R_4$ is hydrogen.

In the instant invention the term "loweralkyl" is intended to include those alkyl groups containing from 1- to 3-carbon atoms. Exemplary of such groups are methyl, ethyl, propyl and isopropyl.

The term "loweralkoxy" is intended to include those alkoxy groups containing from 1 to 3 carbon atoms in either a straight or branched configuration. Exemplary of such groups are methoxy, ethoxy, propoxy, and isopropoxy.

The term "loweralkanoyl" is intended to include those alkanoyl groups containing 2 or 3 carbon atoms exemplified by acetyl and propionyl.

The compounds of the instant invention may be prepared by any one of several processes. The most general process is outlined in the following reaction scheme.

Reaction Scheme 1

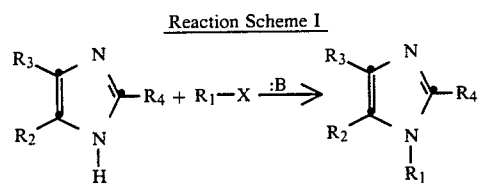

wherein X is a halogen preferably chlorine or bromine. In the foregoing reaction a 1-unsubstituted but otherwise appropriately substituted imidazole is reacted with a halogen substituted $R_1$ group in the presence of a base to prepare the desired 1-substituted imidazole. The reaction is carried out in a solvent which may be any polar aprotic organic solvent such as acetone, dimethylformamide, acetonitrile, dioxane, and the like in the presence of a base. The base may be any non-nucleophilic organic or inorganic base since its purpose is merely to neutralize the acid produced during the course of the reaction. Suitable inorganic bases are alkali metal bases, such as sodium and potassium carbonates, phosphates, bicarbonates and hydroxides. Suitable organic bases are tertiary amines such as trialkyl substituted amines and cyclic aromatic amines such as collidine. The reaction rate varies greatly with the nature of the proposed substituents at the $R_1$ position, the base being used in the reaction and the solvent. Very reactive substituent and base combinations may be complete in as little as ten minutes and at the other extreme the reaction may take as long as two weeks. Most reactions are however complete in from 1 to 100 hours. The reaction is carried out at a temperature of from room temperature to 100° C. or to the reflux temperature of the solvent system being used. The products of the reaction are isolated using techniques known to those skilled in the art.

An alternate procedure for preparing the imidazole compounds wherein $R_2$ is amino and $R_3$ is carbamoyl is outlined in the following reaction scheme:

Reaction Scheme 2

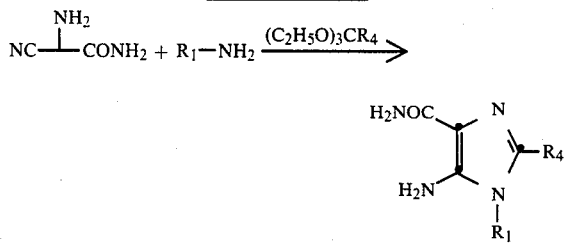

wherein $R_4$ is hydrogen, loweralkyl, or phenyl. The above reaction is carried out in a non-polar aprotic solvent system as described in the preceding reaction scheme. The reaction is carried out by first combining the aminocyanoacetamide and triethylorthoformate in the solvent and stirring at from room temperature to 100° C. or to the reflux temperature of the solvent system being employed for from 10 minutes to 3 hours. Generally this phase of the reaction is complete in from ½ to 1 hour. However, following this reaction period the $R_1$ substituted amine is added to the reaction mixture and the reaction stirred for up to 2 hours at from room temperature to 100° C. or the reflux temperature of the reaction system. The reaction is oftentimes very fast being evidenced by the immediate production of a precipitate and the product may be isolated immediately. However, generally to insure that the reaction is complete, stirring and heating are continued for a short time. The products of the reaction are isolated using techniques known to those skilled in the art.

The novel compounds of this invention are orally administered to poultry for the control and prevention of coccidiosis. Any number of conventional methods are suitable for administering the coccidiostats of this invention to poultry, as for example, they may be given in the poultry feed. The actual quantity of the coccidiostats administered to the poultry in accordance with this invention will vary over a wide range and be adjusted to individual needs, depending upon species of the coccidia involved and severity of the infection. The limiting criteria are that the minimum amount is sufficient to control cocciodiosis and the maximum amount is such that the coccidiostat does not result in any undesirable effects.

A feed typically contains from about 0.0001 to about 0.2 percent, preferably from about 0.001 to about 0.1 percent, by weight of one of the coccidiostats of this invention. The optimum levels will naturally vary with the specific compound utilized and species of Eimeria involved, and can be readily determined by one skilled in the art. Levels of the 5-amino and substituted amino imidazoles of this invention, in poultry feed of from about 0.001 percent to about 0.1 percent by weight of the diet are especially useful in controlling the pathology associated with *E. tenella*, as well as the intestinal dwelling species.

Depending on the compound employed, levels of 0.001 percent to 0.006 percent possess the novel effects of reducing the number of oocysts passed in the droppings of infected chickens and/or inhibiting the subsequent division and maturation to infectivity, scientifically designated as the process of sporulation. Thus, the combination of prevention of pathology, coupled with the inhibiting effect on the reproductive product of these organisms, the oocysts, present a unique two-fold method for the control of coccidiosis in poultry.

The quantity or concentration of a novel coccidiostat of this invention in any admixture in which it is administered to the poultry will, of course, vary in accordance with the type of admixture utilized.

Of the various methods of administering the coccidiostats of this invention to poultry, they are most conveniently administered as a component of a feed composition. The novel coccidiostats may be readily dispersed by mechanically mixing the same in finely ground form with the poultry feedstuff, or with an intermediate formulation (premix) that is subsequently blended with other components to prepare the final poultry feedstuff that is fed to the poultry. Typical components of poultry feedstuffs include molasses, fermentation residues, corn meal, ground and rolled oats, wheat shorts and middlings, alfalfa, clover and meat scraps, together with mineral supplements such as bone meal and calcium carbonate and vitamins.

The following non-limiting examples will serve to further illustrate the instant invention.

EXAMPLE 1

Preparation of 1-substituted-5-aminoimidazole-4-carboxamides (Method A)

A mixture of 5-aminoimidazole-4-carboxamide hydrochloride, potassium carbonate, alkyl halide, and acetone were refluxed together for from 3 to 168 hours, the solvent was concentrated to about 1/6 of the original volume and the mixture filtered. The solid was washed with acetone, slurried in water, and filtered. The remaining solid was slurried in water, treated with glacial acetic acid to remove residual potassium carbonate, and filtered. The filter cake was washed with water, acetone, and ether to provide the desired 1-substituted-5-aminoimidazole-4-carboxamide. (Table 1).

TABLE 1

| alkyl halide (R₁—X) (X = halogen) | Wt (g) | [imidazole·HCl structure] Wt (g) | K₂CO₃ Wt (g) | acetone vol (ml) | reflux time (hr) | yield (g) [product structure] | m.p. (°C) |
|---|---|---|---|---|---|---|---|
| 4-Cl-benzyl chloride | 7.25 | 4.9 | 16.6 | 300 | 48 | 4.0 | 271–273[1] |
| 2,3-diCl-benzyl chloride | 2.9 | 1.95 | 6.6 | 125 | 46 | 1.98 | 251–252[2] |
| 2,3,4-triCl-benzyl chloride | 8.8 | 4.9 | 16.6 | 300 | 65 | 5.15 | 241–244 |
| 3,5-diCl-benzyl chloride | 3.5 | 1.95 | 6.6 | 125 | 64 | 1.30 | 247–248[2] |
| 3,4,5-triCl-benzyl chloride | 6.61 | 3.09 | 10.5 | 250 | 26 | 2.5 | 286–287.5[2] |
| 4-F-2-Cl-benzyl chloride | 6.5 | 4.9 | 16.6 | 300 | 20 | 5.8 | 237–241 |
| 4-NO₂-benzyl chloride | 7.15 | 4.9 | 16.6 | 300 | 3 | 1.2 | 219–221 |
| 3-CF₃-benzyl chloride | 3.5 | 1.95 | 6.6 | 125 | 48 | 1.54 | 192.5–194[2] |
| phenethyl bromide | 8.3 | 4.9 | 16.6 | 300 | 90 | 1.95 | 206–209 |
| phenacyl chloride | 6.95 | 4.9 | 16.6 | 300 | 21 | 2.3 | 197–215 |

[1] In this case crude solid product was recrystallized from 65 ml acetic acid-water (10:3 v/v).
[2] Melting point after recrystallization from aqueous ethanol.

Other compounds which can be prepared by Method A:

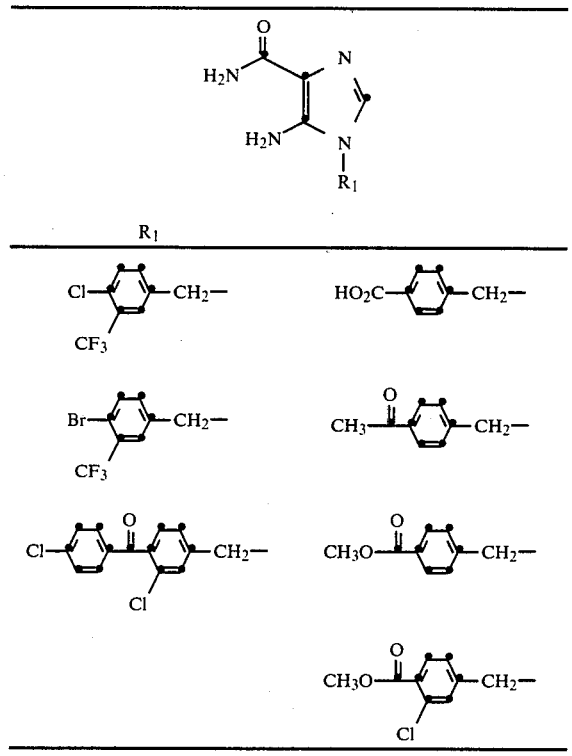

EXAMPLE 2

Preparation of 1-substituted-5-aminoimidazole-4-carboxamides (Method B)

A mixture of aminocyanoacetamide and triethyl orthoformate in acetonitrile was refluxed for 30–55 minutes. The mixture may be filtered if a small amount of precipitate forms. A primary amine, $R_1NH_2$, was added and the mixture was refluxed for 15–30 minutes. The mixture was cooled and product collected by filtration (Table 2) or isolated by chromatography.

TABLE 2

| NC-CH(NH$_2$)-CONH$_2$ (g) | (EtO)$_3$CH (g) | CH$_3$CN (ml) | reflux time (min.) | amine R$_1$—NH$_2$ | weight amine (g) | additional reflux time (min.) | yield (g) | melting point (°C.) |
|---|---|---|---|---|---|---|---|---|
| 2.00 | 3.29 | 30 | 45 | C$_6$H$_5$—NH$_2$ | 1.88 | 15 | 1.5 | 190–194 |
| 2.00 | 3.29 | 30 | 30 | 4-CH$_3$-C$_6$H$_4$—NH$_2$ | 2.16 | 30 | 3.1 | 242.5–254 (dec) |
| 2.00 | 3.30 | 30 | 30 | 4-Cl-C$_6$H$_4$—NH$_2$ | 2.58 | 30 | 1.7 | 262–263 |
| 1.48 | 2.48 | 22 | 45 | 3,4-Cl$_2$-C$_6$H$_3$—NH$_2$ | 2.40 | 45 | 1.97 | |
| 2.56 | 4.21 | 25 | 45 | 4-CH$_3$O-C$_6$H$_4$—NH$_2$ | 3.18 | 20 | 3.55 | 236–238 |

TABLE 2-continued

| | | | | Structure | | | | |
|---|---|---|---|---|---|---|---|---|
| 2.00 | 3.29 | 30 | 45 | 2,4-dichloro-phenoxy-chloroaniline | 5.13 | 15 | 4.4 | 188–191[1] |
| 0.297 | 0.489 | 4.5 | 45 | 3,4-dichlorobenzylamine | 0.528 | 15 | 0.609 | 238–240 |
| 0.531 | 0.877 | 8.0 | 45 | 3,4-dichlorophenethylamine | 1.02 | 15 | 0.885 | 235–237 |
| 1.48 | 2.48 | 22 | 45 | 1-(3,4-dichlorophenyl)ethylamine | 2.85 | 15 | 2.66 | 247–249 |
| 2.00 | 3.29 | 30 | 50 | 2-aminopyridine | 1.92 | 15 | 1.05 | 198.5–200[1] |
| 0.273 | 0.454 | 4.1 | 45 | 4-chlorophenoxy-chloro-benzylamine | 0.751 | 15 | 0.340 | 199–200 |
| 1.24 | 2.05 | 18 | 45 | 4-chlorophenylthio-chloro-benzylamine | 3.6 | 15 | 3.16 | 201–202 |
| 0.500 | 0.820 | 8.0 | 45 | 1-naphthylmethylamine | 0.785 | 15 | 0.831 | 258–260 |
| 0.870 | 1.43 | 14 | 45 | 2-naphthylmethylamine | 1.38 | 15 | 1.62 | 264–270 |
| 0.700 | 1.25[2] | 12 | 45 | 3,4-dichlorobenzylamine | 1.24 | 15 | 1.22[3] | 275 |
| 0.556 | 0.89 | 8.0 | 45 | 4-chlorophenylthio-2,6-dichloro-benzylamine | 1.79 | 15 | 1.24 | 221–222 |
| 0.314 | 0.49 | 4.0 | 45 | 2,4-dichlorobenzoyl-methylbenzylamine | 0.845 | 15 | 0.741 | 229–230 |
| 0.332 | 0.52 | 4.2 | 45 | 4-chlorobenzoyl-dimethyl-benzylamine | 0.830 | 30 | 0.592 | 226–227 |

| 0.117 | 0.183 | 1.5 | 45 | 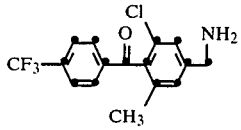 | 0.350 | 45 | 0.121 | 221–223 |
[1]Melting point after recrystallization from 98:2 (v/v) ethanol-benzene.
[2]Weight of triethylorthoacetate.
[3]Yield of 1-(3,4-dichlorobenzyl)-2-methyl-5-aminoimidazole-4-carboxamide, isolated in two crops, triturated with 20 ml of hot acetonitrile and dried.
Other compounds which can be prepared by Method B:
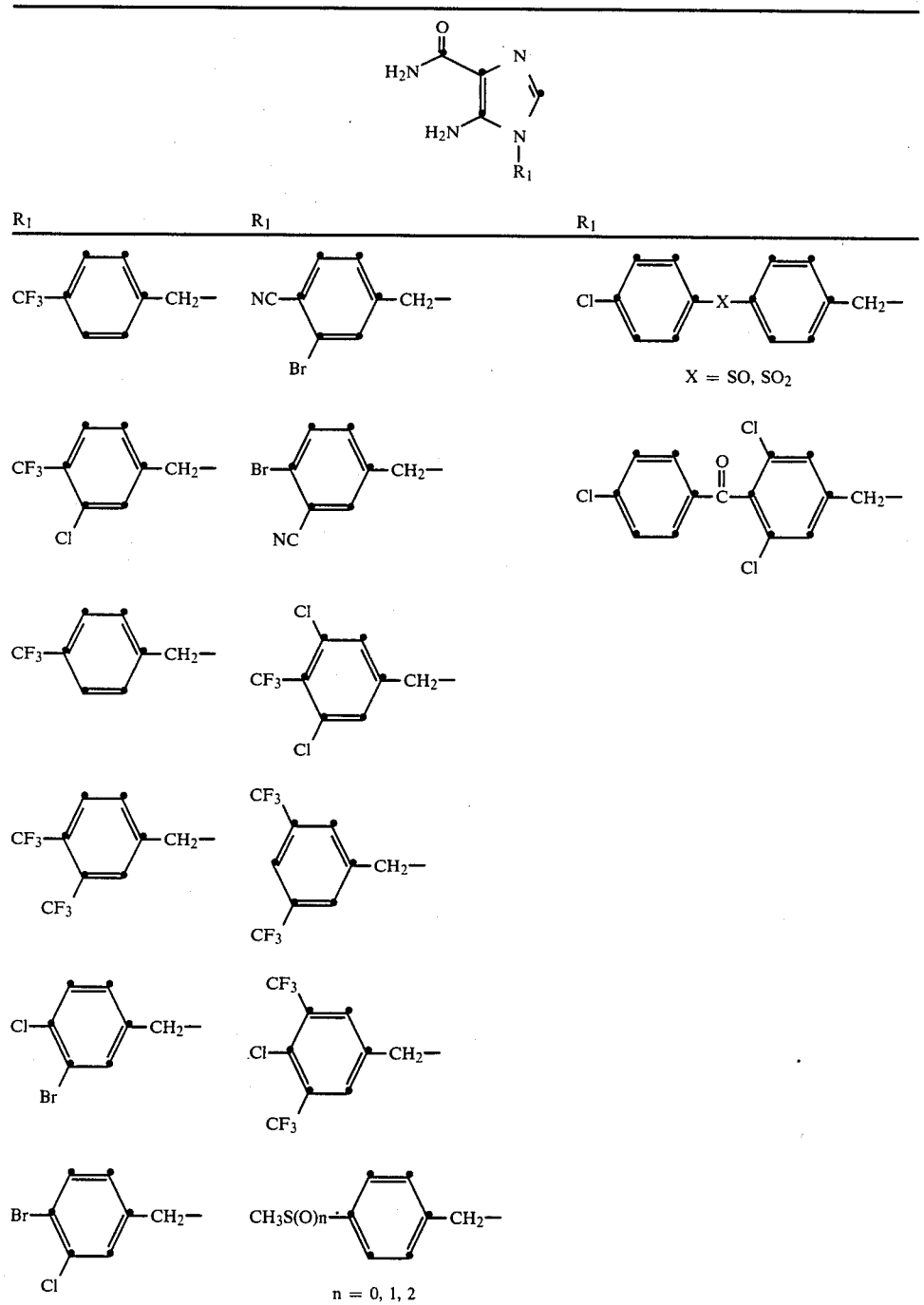

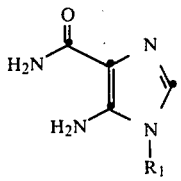

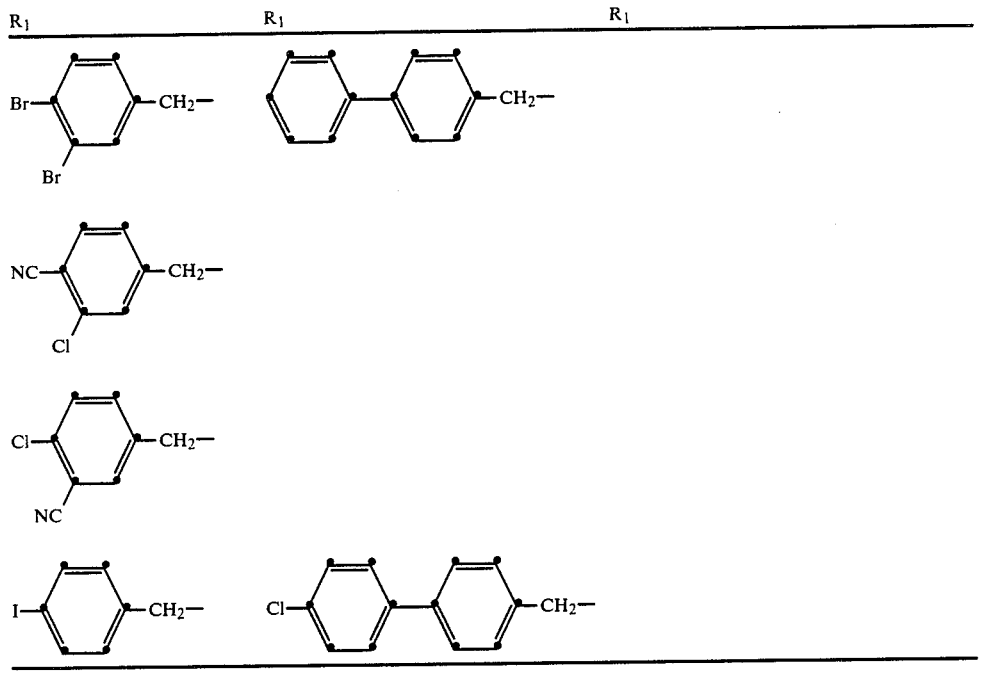

EXAMPLE 3

Preparation of 1-(m-cyanobenzyl)-5-aminoimidazole-4-carboxamide

A mixture of 5-aminoimidazole-4-carboxamide (5.00 g), potassium carbonate (12.0 g), and α-bromo-m-tolunitrile (9.80 g) were refluxed in acetone (300 ml) for 24 hours under a nitrogen atmosphere. The mixture was cooled to room temperature and filtered. The solid residue was washed with acetone and the combined filtrates were evaporated to dryness. The residual solid was dissolved in acetone (50 ml), concentrated to a volume of 20 ml in vacuo, and diluted with diethyl ether (100 ml) to provide a gum. The solvent was decanted from the residue and deposited crystals of crude product on standing. The gum was triturated twice with acetone, and the acetone layers were combined with the above crystals, and evaporated to provide 5.9 g of a dark gum. The gum was dissolved in methanol (100 ml), filtered, added to 100 ml. E. Merck 7734 silica gel, and evaporated to dryness in vacuo. The product on silica gel was placed on top of a column of 1200 ml E. Merck 7734 silica gel and eluted with 9:1 v/v methylene chloride/methanol. After a forerun of 1.0 l, 400 ml fractions were collected and fractions 8-11 and 12-15 were combined separately and evaporated to dryness. The solid product from fractions 8-11 was triturated with a small volume of acetone and filtered. The filtrate was combined separately with the product from fractions 12-15 and evaporated to dryness. The product was recrystallized from methanol to provide 320 mg of 1-(m-cyanobenzyl)-5-aminoimidazole-4-carboxamide, m.p. 246°-247° C.

EXAMPLE 4

Preparation of 1-(4-chloro-3-trifluoromethylbenzyl)-5-aminoimidazole-4-carboxamide A mixture of 5-aminoimidazole-4-carboxamide hydrochloride (5.0 g), K$_2$CO$_3$ (16.5 g), and a 9:1 w/w mixture of α,4-chloro-3-trifluoromethyltoluene and α,2-dichloro-3-trifluoromethyltoluene were refluxed in acetone (300 ml) for 4 days. Solvent was concentrated in vacuo, the residue was diluted with water, and the solution was extracted with ethyl acetate. The combined ethyl acetate extracts were washed with brine, 0.5N acetic acid, and brine, dried, treated with activated charcoal, and filtered. The filtrate was concentrated to provide a first crop of 3.40 g. The filtrate was diluted with ether to provide a second crop of 2.07 g, and the remaining filtrate was diluted with hexane to provide a third crop of 0.25 g. The second and third crops were combined, dissolved in aqueous ethanol, diluted with water, and concentrated to provide 0.97 g of solid. Further concentration of the filtrate provided an additional 0.43 g. The samples weighing 3.40 g, 0.97 g, and 0.43 g were combined, treated with hot 7.5% methanol in ethyl acetate, and diluted with 50 ml ethyl acetate. The resulting solution was chromatographed on a column of 500 ml silica gel, eluted with 7.5% methanol in ethyl acetate followed by 10% methanol in ethyl acetate. A total of 150 fractions of 20 ml each were collected at a flow rate of about 10 ml/min. Fractions 60-118 were combined and evaporated to provide 3.53 g solid. The product was dissolved in 100 ml of boiling ethanol, treated with activated charcoal, and filtered. The filtrate was concentrated to provide a first crop of crystals, and further concentration of the filtrate provided a second crop. The two crops were combined and recrystallized from 50 ml of ethanol to provide 1.99 g 1-(4-chloro-3-trifluoromethylbenzyl)-5-aminoimidazole-4-carboxamide, m.p. 230.5°–232.5° C.

What is claimed is:

1. A compound having the formula

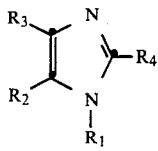

wherein:

$R_1$ is mono-substituted phenyl or mono-substituted phenyl alkyl wherein the substituent is trifluoromethyl, loweralkanoyl, nitro, carboxy, carbalkoxy, acetamido, loweralkylthio, loweralkylsulfinyl, loweralkylsulfonyl or

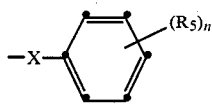

wherein n is from 1 to 5, $R_5$ is as defined as below and X is O, S, SO, $SO_2$, $CH_2$, CO, CHOH, CHCN or C=$NR_6$ where $R_6$ is hydrogen, loweralkyl, hydroxy, loweralkoxy, amino, loweralkylamino, or diloweralkylamino;

$R_1$ is also polysubstituted phenyl or polysubstituted phenylalkyl wherein the substituents are two to five $R_5$ wherein $R_5$ is independently halogen, cyano, trifluoromethyl, loweralkanoyl, nitro, loweralkyl, loweralkoxy, carboxy, carbalkoxy, trifluoromethoxy, acetamido, loweralkylthio, loweralkylsulfinyl, loweralkylsulfonyl, trichlorovinyl, trifluoromethylthio, trifluoromethylsulfinyl, or trifluoromethylsulfonyl or

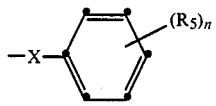

where $R_5$, X, and n are as defined above;

provided that if the monosubstituent or one of the polysubstituents is halogen, loweralkyl or loweralkoxy, such groups are in positions other than those ortho to the positions of attachment of the phenyl to the imidazole or the alkyl, which is in turn attached to the imidazole;

$R_1$ may also be phenacyl, pyridyl, pyridylmethyl, naphthyl, naphthylmethyl, quinolyl, or quinolylmethyl;

$R_2$ is amino, mono or diloweralkylamino, acetamido, acetimido, ureido, formamido, formimido or guanidino;

$R_3$ is carbamoyl, cyano, carbazoyl, amidino or N-hydroxycarbamoyl; and $R_4$ is hydrogen, loweralkyl, hydroxy, amino, mono- or diloweralkylamino, phenyl, cyano, loweralkoxy, loweralkanoyloxy, loweralkylthio, loweralkylsulfinyl, or loweralkylsulfonyl.

2. The compound of claim 1 wherein $R_1$ is mono-substituted phenyl or mono-substituted benzyl wherein the substituent is trifluoromethyl, phenoxy, benzoyl, phenylthio, phenylsulfinyl, phenylsulfonyl, halo or methyl or trifluoromethyl substituted phenoxy, halo or methyl or trifluoromethyl substituted phenylthio, halo or methyl or trifluoromethyl substituted phenyl sulfinyl, halo or methyl or trifluoromethyl substituted phenyl sulfonyl, halo or methyl or trifluoromethyl substituted benzoyl or halo or methyl, or trifluoromethyl substituted phenylhydroxymethyl;

$R_1$ is also di- or trisubstituted phenyl or di- or trisubstituted benzyl wherein the substituents are halogen, cyano, methyl trifluoromethyl, phenoxy, benzoyl, phenylthio, phenylsulfinyl, phenylsulfonyl, halo or methyl or trifluoromethyl substituted phenoxy, halo or methyl or trifluoromethyl substituted phenylthio, halo or methyl or trifluoromethyl substituted phenylsulfinyl, halo or methyl or trifluoromethyl substituted phenylsulfonyl, or halo or trifluoromethyl substituted benzoyl or halo or methyl, or trifluoromethyl substituted phenylhydroxymethyl;

provided that if the monosubstituent or one of the disubstituents is halogen, such group is in a position other than those ortho to the position of attachment of the phenyl to the imidazole or to the methylene which is in turn attached to the imidazole;

$R_2$ is amino or mono or diloweralkylamino;

$R_3$ is carbamoyl; and $R_4$ is hydrogen.

3. The compound of claim 2 wherein $R_1$ is substituted phenyl or substituted benzyl wherein the substituents are 2 to 3 in the meta or para positions and are halo cyano, methyl, trifluoromethyl, halo, methyl or trifluoromethyl phenoxy, halo or methyl or trifluoromethyl phenylthio, halo, or methyl or trifluoromethyl phenyl sulfinyl, halo or methyl or trifluoromethyl phenyl sulfonyl, halo or methyl or trifluoromethyl benzoyl or halo or methyl, or trifluoromethyl substituted phenylhydroxymethyl;

$R_2$ is amino;

$R_3$ is carbamoyl; and $R_4$ is hydrogen.

4. The compound of claim 1 which is 5-amino-1-(3,4,5-trichlorobenzyl)imidazole-4-carboxamide.

5. The compound of claim 1 which is 5-amino-1-([4-(4-chlorophenylthio)-3-chlorobenzyl]imidazole-4-carboxamide.

6. The compound of claim 1 which is 5-amino-1-[4-(4-chlorophenoxy)-3-chlorobenzyl]imidazole-4-carboxamide.

7. The compound of claim 1 which is 5-amino-1-[4-(4-chlorophenylthio)-3,5-dichlorobenzyl]imidazole-4-carboxamide.

8. The compound of claim 1 which is 5-amino-1-[4-(4-chlorobenzoyl)-3-chlorobenzyl]imidazole-4-carboxamide.

9. The compound of claim 1 which is 5-amino-1-[4-(4-chlorobenzoyl)-3,5-dichlorobenzyl]imidazole-4-carboxamide.

10. The compound of claim 1 which is 5-amino-1-(4-[4-trifluoromethylbenzoyl]-3-chloro-5-methylbenzyl)imidazole-4-carboxamide.

11. The compound of claim 1 which is 5-amino-1-(4-[4-chlorobenzoyl]-3-chloro-5-methylbenzyl)imidazole-4-carboxamide.

12. A composition useful for the prevention and treatment of coccidiosis which comprises an inert carrier and an amount of a compound of claim 1 effective to prevent or treat coccidiosis.

13. A method for preventing or treating coccidiosis which comprises administering to an animal in need of such treatment an amount of a compound of claim 1 effective to prevent or treat coccidiosis.

* * * * *